United States Patent
Behrooz et al.

(10) Patent No.: US 11,915,419 B1
(45) Date of Patent: Feb. 27, 2024

(54) AUTO-NORMALIZATION FOR MACHINE LEARNING

(71) Applicant: Verily Life Sciences LLC, South San Francisco, CA (US)

(72) Inventors: Ali Behrooz, South San Francisco, CA (US); Cheng-Hsun Wu, San Bruno, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 424 days.

(21) Appl. No.: 17/358,621

(22) Filed: Jun. 25, 2021

Related U.S. Application Data

(60) Provisional application No. 62/705,403, filed on Jun. 25, 2020.

(51) Int. Cl.
*G06T 7/00* (2017.01)
*G16H 30/40* (2018.01)
*G06N 3/08* (2023.01)

(52) U.S. Cl.
CPC ............ *G06T 7/0012* (2013.01); *G06N 3/08* (2013.01); *G16H 30/40* (2018.01); *G06T 2207/20081* (2013.01); *G06T 2207/20084* (2013.01)

(58) Field of Classification Search
None
See application file for complete search history.

(56) References Cited

U.S. PATENT DOCUMENTS

| | | | |
|---|---|---|---|
| 2016/0217368 A1 | 7/2016 | Ioffe et al. | |
| 2018/0137642 A1 | 5/2018 | Malisiewicz et al. | |
| 2018/0232883 A1* | 8/2018 | Sethi | G16H 30/40 |
| 2022/0246301 A1* | 8/2022 | Choi | G16H 50/50 |

FOREIGN PATENT DOCUMENTS

| | | |
|---|---|---|
| CN | 106919903 | 12/2019 |
| WO | 2019081545 | 5/2019 |

OTHER PUBLICATIONS

Badrinarayanan et al., "Segnet: A deep convolutional encoder-decoder architecture for image segmentation", IEEE transactions on pattern analysis and machine intelligence 39.12 (2017): 2481-2495; arXiv:1511.00561.

(Continued)

*Primary Examiner* — Leon Flores
(74) *Attorney, Agent, or Firm* — Kilpatrick Townsend & Stockton LLP

(57) ABSTRACT

Systems and methods for using a prediction model jointly with a normalization model to provide prediction results are provided. One example method includes receiving an input image of a tissue sample of a patient and generating a normalized image by applying a normalization model on the input image. The normalization model is configured to generate normalized data using input data for a prediction model, and the prediction model is configured to generate prediction results using normalized data generated by the normalization model. The normalization model and the prediction model are jointly trained. The method further includes generating a prediction of disease severity for the patient by applying the prediction model on the normalized image.

20 Claims, 6 Drawing Sheets

(56) References Cited

OTHER PUBLICATIONS

Bejnordi et al., "Diagnostic assessment of deep learning algorithms for detection of lymph node metastases in women with breast cancer", Jama 318.22 (2017): 2199-2210.
Chaurasia et al., "Linknet: Exploiting encoder representations for efficient semantic segmentation", 2017 IEEE Visual Communications and Image Processing (VCIP). IEEE, 2017; arXiv:1707.03718.
Chen et al., "Deeplab: Semantic image segmentation with deep convolutional nets, atrous convolution, and fully connected crfs", IEEE transactions on pattern analysis and machine intelligence 40.4 (2017): 834-848; arXiv:1606.00915.
Cubuk et al., "Autoaugment: Learning augmentation policies from data", arXiv preprint arXiv:1805.09501 (2018).
Devries et al., "Improved regularization of convolutional neural networks with cutout", arXiv preprint arXiv:1708.04552 (2017).
Lin et al., "Refinenet: Multi-path refinement networks for high-resolution semantic segmentation", Proceedings of the IEEE conference on computer vision and pattern recognition. 2017; arXiv:1611.06612.
Paszke et al., "Enet: A deep neural network architecture for real-time semantic segmentation", arXiv preprint arXiv:1606.02147 (2016).
Ronneberger et al., "U-net: Convolutional networks for biomedical image segmentation", International Conference on Medical image computing and computer-assisted intervention. Springer, Cham, 2015.
Salimans et al., "Improved techniques for training gans", arXiv preprint arXiv:1606.03498 (2016).
Valenza, "Linear algebra: an introduction to abstract mathematics", Springer Science & Business Media, 2012, p. 22.
Wan et al., "Regularization of neural networks using dropconnect", International conference on machine learning. PMLR, 2013.
Wang et al., "Enaet: Self-trained ensemble autoencoding transformations for semi-supervised learning", arXiv preprint arXiv:1911.09265 2 (2019).
Xie et al., "Unsupervised data augmentation for consistency training", arXiv preprint arXiv:1904.12848 (2019).
Zagoruyko et al., "Wide residual networks", British Machine Vision Conference, 2016.
Zhang et al., "mixup: Beyond empirical risk minimization", arXiv preprint arXiv:1710.09412 (2017).
Zhao et al., "Pyramid scene parsing network", Proceedings of the IEEE conference on computer vision and pattern recognition. 2017; arXiv:1612.01105.
Zhong et al., "Random erasing data augmentation", arXiv preprint arXiv:1708.04896, 2017.

* cited by examiner

FIG. 5

AUTO-NORMALIZATION FOR MACHINE LEARNING

CROSS-REFERENCE TO RELATED APPLICATIONS

This application claims priority to U.S. Provisional Patent Application No. 62/705,403, filed Jun. 25, 2020 entitled "Auto-Normalization For Machine Learning," the entirety of which is hereby incorporated by reference.

TECHNICAL FIELD

The present application generally relates to artificial intelligence and machine learning, and more particularly relates to building and jointly training machine learning models including a normalization model and a prediction model to reduce the size of labeled training data and improve the performance and accuracy of the prediction model.

BACKGROUND

Machine learning models can be used to perform one or more prediction functions such as image or signal classification, recognition, or segmentation based on input data. Machine learning algorithms build and train the machine learning models based on training data that include training inputs and outputs corresponding to the training inputs, also referred to as "labeled training data." In this way, machine learning models learn to make predictions without being explicitly programmed with the rules to do so. To ensure the accuracy of the machine learning models, especially complicated machine learning models, a large amount of training data is typically utilized for the training.

Obtaining labeled training data, however, is time-consuming and often requires experts' involvement. In addition, available training data typically cannot fully capture the entire range of variability in the real-world input data. For example, for a machine learning model configured to classify an input image, the training images might not cover all the color variations, lighting condition variations, or the bit-depth variations, among other sources of variations, of the input images. As a result, training machine learning models using insufficient training data leads to the low prediction accuracy of the machine learning models.

SUMMARY

Various examples are described for training a normalization model along with a prediction model to reduce the training sample size and improve the prediction accuracy of the prediction model. One example method includes receiving an input image of a tissue sample of a patient and generating a normalized image by applying a normalization model on the input image. The normalization model is configured to generate normalized data using input data for a prediction model, and the prediction model is configured to generate prediction results using normalized data generated by the normalization model. The normalization model and the prediction model are jointly trained by comparing a first set of prediction results generated by the prediction model using a first set of normalized training inputs generated by applying the normalization model to training inputs in a set of training samples once and a second set of prediction results generated by the prediction model using a second set of normalized training inputs generated by applying the normalization model to the training inputs more than once. The method further includes generating a prediction of disease severity for the patient by applying the prediction model on the normalized image.

One example system includes at least one processor and at least one non-transitory computer-readable medium having processor-executable instructions stored thereupon, which, when executed by the at least one processor, cause the processor to perform operations. The operations include receiving an input image of a tissue sample of a patient and generating a normalized image by applying a normalization model on the input image. The normalization model is configured to generate normalized data using input data for a prediction model, and the prediction model is configured to generate prediction results using normalized data generated by the normalization model. The normalization model and the prediction model are jointly trained by comparing a first set of prediction results generated by the prediction model using a first set of normalized training inputs generated by applying the normalization model to training inputs in a set of training samples once and a second set of prediction results generated by the prediction model using a second set of normalized training inputs generated by applying the normalization model to the training inputs more than once. The operations further include generating a prediction of disease severity for the patient by applying the prediction model on the normalized image.

One example non-transitory computer-readable medium includes processor-executable instructions to cause a processor to perform operations. The operations include receiving an input image of a tissue sample of a patient and generating a normalized image by applying a normalization model on the input image. The normalization model is configured to generate normalized data using input data for a prediction model, and the prediction model is configured to generate prediction results using normalized data generated by the normalization model. The normalization model and the prediction model are jointly trained by comparing a first set of prediction results generated by the prediction model using a first set of normalized training inputs generated by applying the normalization model to training inputs in a set of training samples once and a second set of prediction results generated by the prediction model using a second set of normalized training inputs generated by applying the normalization model to the training inputs more than once. The operations further include generating a prediction of disease severity for the patient by applying the prediction model on the normalized image.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of certain examples.

FIG. 5 shows examples of input images and normalized input images generated by a trained normalization model applied to National Institute of Standards and Technology (MNIST) image data, according to certain aspects of the present disclosure.

DETAILED DESCRIPTION

Figure 1:
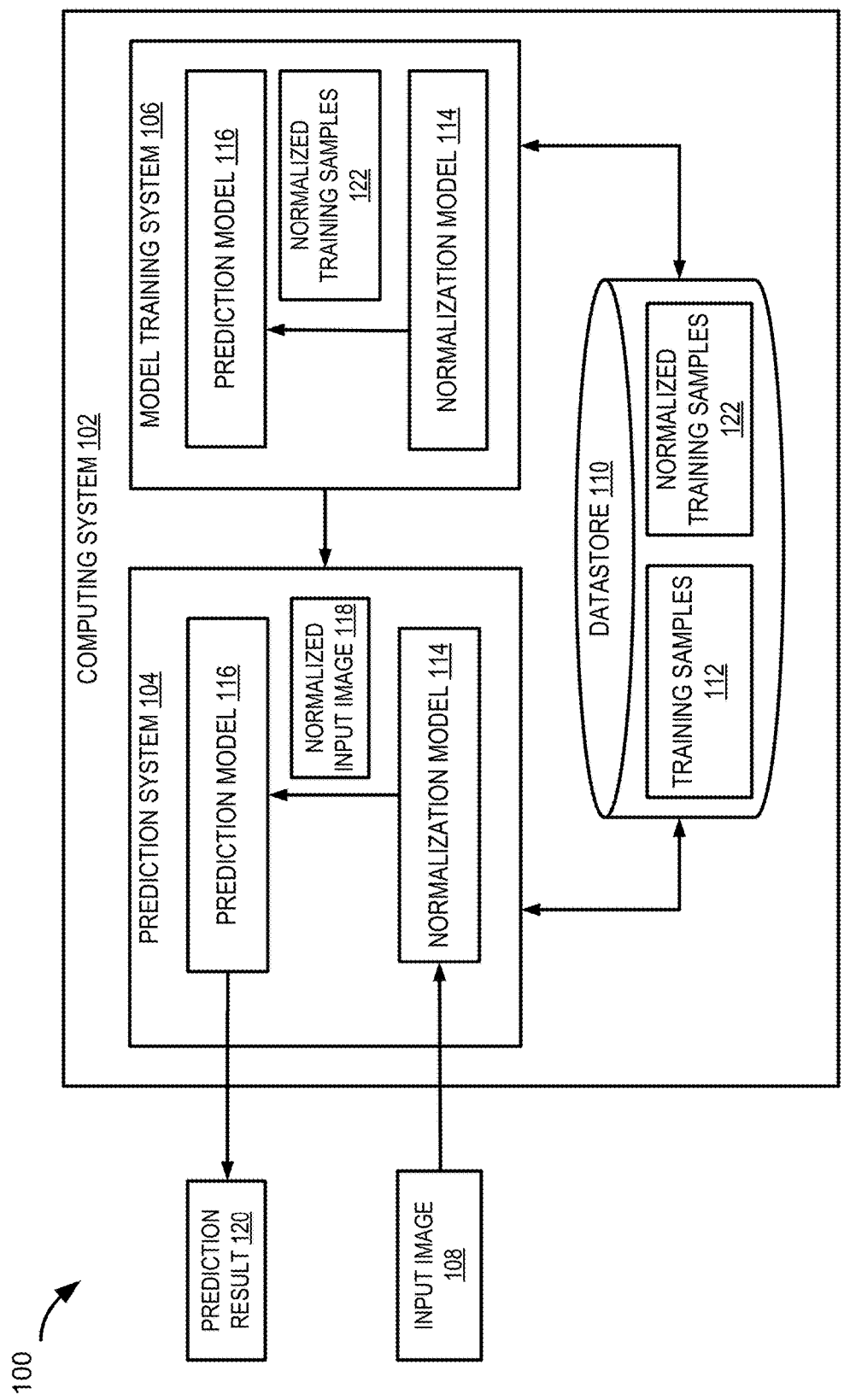
FIG. 1 shows an example of a computing environment in which a normalization model and a prediction model can be jointly trained and applied to generate a prediction for a given input, according to certain aspects of the present disclosure.

Examples are described herein in the context of building and training a prediction model jointly with a normalization model to normalize the input data for the prediction model. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, a set of training samples are obtained for a prediction model configured to generate prediction results for a given input. The training samples include labeled training samples and unlabeled training samples. A labeled training sample includes a training input and a corresponding training output or label describing what the prediction should be, whereas an unlabeled training sample includes the training input, but does not include the corresponding training output. The prediction model is extended to include a normalization model. The normalization model is configured to normalize the input data to the prediction model to remove variations in the input data irrelevant to the prediction task and highlight features utilized by the prediction model.

For instance, for a prediction model configured for classifying an input image of a single digit into a number between 0 to 9, the color of the digit in the input image is irrelevant to the prediction task and will be normalized to a fixed color or a small range of colors by the normalization model before being fed to the prediction model. Without the normalization model, the prediction model would need to be trained using training images containing a digit in various colors so that the prediction model can accurately predict the number when presented with input images in different colors. By removing the irrelevant color variations in the input image, the prediction model can focus on the features useful for the prediction, such as the edge information in the image. The normalized data generated by the normalization model is provided to the prediction model for generating prediction results.

In this example, the training samples are utilized to jointly train the normalization model and the prediction model. In particular, a loss function is formulated to include loss terms generated for the normalization model and the prediction model based on the training samples. The training process adjusts the parameters of the normalization model and the prediction model so that the loss function is minimized. For instance, for unlabeled training samples, the loss function includes an idempotence loss term measuring the difference between a first set of prediction results and a second set of prediction results generated by the prediction model. The first set of prediction results are generated using a first set of normalized training inputs generated by applying the normalization model to the training inputs once. The second set of prediction results are generated using a second set of normalized outputs generated by applying the normalization model to the training inputs more than once.

By minimizing the loss function containing the idempotence loss term, the normalization model is trained to have idempotence property. In other words, the output of the normalization model applied once on the input data is optimized to be the same as the output of the normalization model applied more than once on the same input data. In this way, the normalization model can be trained to normalize the input data in a way that removes irrelevant variations in the input data that are not used by the prediction model (e.g., color variations, texture variations) and highlights features that are relied on by the prediction model (e.g., edge information).

The loss function further includes other terms for the prediction model and the normalization model. For example, the loss function also includes a loss term measuring the entropy of the prediction results for the unlabeled training samples. The entropy loss term and the idempotence loss term form the loss terms for the unlabeled training samples. For labeled training samples, the loss term is constructed using any standard loss between the training outputs or labels in the training samples and the prediction results generated by the prediction model using the training inputs. The standard loss can include, for example, cross entropy loss, L1 loss, or L2 loss. The loss terms for the labeled data and unlabeled data are combined to determine the loss function for the training.

The normalization model and the prediction model that minimize the loss function become the trained normalization model and the trained prediction model. For a given input (e.g., an input image), the trained normalization model generates a normalized input (e.g., a normalized input image). The normalized input is fed into the trained prediction model to generate prediction results.

In another example, the trained normalization model (with parameters fixed or frozen) is utilized to generate normalized training samples for a second prediction model that utilizes similar features as the trained prediction model. The normalized training samples are then utilized to train the second prediction model. In this way, the training of the second prediction model can be performed using fewer training samples than training the second prediction model without using the normalized training samples.

The technology presented herein improves the training of machine learning models. Compared with existing machine learning models, a normalization model is added to a prediction machine learning model. The normalization model can remove irrelevant variations in the input data and highlight features for the prediction model. As such, the prediction model only needs to be trained to focus on the features useful for the prediction and does not need to be trained using data containing variations of irrelevant features. Accordingly, the amount of labeled training data can be significantly reduced without sacrificing the prediction accuracy of the prediction model. Or conversely, the accuracy of the prediction model can be significantly improved using the same amount of labeled training data as the traditional machine learning models. Furthermore, training the prediction model using the normalized input data also reduces the computational complexity and memory usage of the training process because only a small amount of normalized input data are needed for the training.

This illustrative example is given to introduce the reader to the general subject matter discussed herein and the disclosure is not limited to this example. The following sections describe various additional non-limiting and non-exhaustive examples of building and training a prediction model jointly with a normalization model to normalize the input data for the prediction model.

Referring now to FIG. 1, FIG. 1 shows an example of a computing environment 100 in which a normalization model 114 and a prediction model 116 can be jointly trained and applied to generate a prediction result 120 for a given input, such as an input image 108, according to certain aspects of the present disclosure. The computing environment 100 includes a computing system 102, which can include one or more processing devices that execute or host a prediction system 104 to perform predictions based on input data and a model training system 106 for training the machine learning models used in the prediction. The machine learning models include the normalization model 114 and the prediction model 116. The normalization model 114 is configured to remove irrelevant variations in the input image 108 of the prediction model 116 and to highlight features utilized by the prediction model 116. The prediction model 116 is configured to generate a prediction result 120 for the input image 108, such as classifying the input image 108 into one or more categories, recognizing objects in the input image 108, or segmenting objects or pixels in the input image 108.

The computing environment 100 further includes a datastore 110 for storing data used in training the machine learning models, such as training samples 112. The training samples 112 can include labeled training samples 142 and unlabeled training samples 144. A labeled training sample includes a training input and a corresponding training output or label describing what the prediction should be, whereas an unlabeled training sample includes the training input, but does not include the corresponding training output. The normalized training samples 122 include training samples that are generated by applying the normalization model 114 onto the training samples 112.

In some examples, the prediction system 104 receives an input image 108 for which a prediction result 120 is to be generated. The image can be a medical image, such as a pathology or microscopy image, or a photographic image. To generate the prediction result 120 for the input image 108, the prediction system 104 employs a trained normalization model 114 and a trained prediction model 116. The trained normalization model 114 accepts the input image 108 as an input and outputs a normalized input image 118. The normalized input image 118 is fed into the trained prediction model 116 to generate the prediction result 120.

To obtain the trained normalization model 114 and the trained prediction model 116, the computing system 102 can employ the model training system 106 to build and train these models. For example, the model training system 106 can be configured to jointly train the normalization model 114 and the prediction model 116. In particular, a loss function is formulated to include loss terms generated for the normalization model 114 and the prediction model 116 based on both labeled training data or unlabeled training data. During the training process, the model training system 106 adjusts the parameters of the normalization model 114 and the prediction model 116 so that the loss function is minimized. For instance, for unlabeled training samples, the loss function includes an idempotence loss term measuring the difference between a first set of prediction results and a second set of prediction results generated by the prediction model 116. The first set of prediction results are generated using a first set of normalized training inputs generated by applying the normalization model 114 to the training inputs once. The second set of prediction results are generated using a second set of normalized outputs generated by applying the normalization model 114 to the training inputs more than once.

By minimizing the loss function containing the idempotence loss term, the normalization model is trained to have an idempotence property from the prediction model's perspective. In other words, the output of the normalization model by applying it once on the input data is the same (to the prediction model 116) as the output of the normalization model 114 by applying it more than once on the input data. In this way, the normalization model is trained to normalize the input data in a way that removes irrelevant variations (e.g., color variations, texture variations) and highlights features that are relied on by the prediction model 116 (e.g., edge information).

The loss function further includes other terms for the prediction model 116 and the normalization model 114. For example, the loss function can also include a loss term measuring the entropy of the prediction results for the unlabeled training samples. The entropy loss term and the idempotence loss term form the loss terms for the unlabeled training samples. For labeled training samples, the loss term can be constructed using any loss between the training outputs in the training samples and the prediction results generated using the training inputs. The loss can include, for example, cross entropy loss, L1 loss, or L2 loss. The loss terms for the labeled data and unlabeled data are combined to determine the loss function for the training Additional details about training the normalization model 114 and the prediction model 116 are provided below with regard to FIGS. 2-5.

Figure 2:
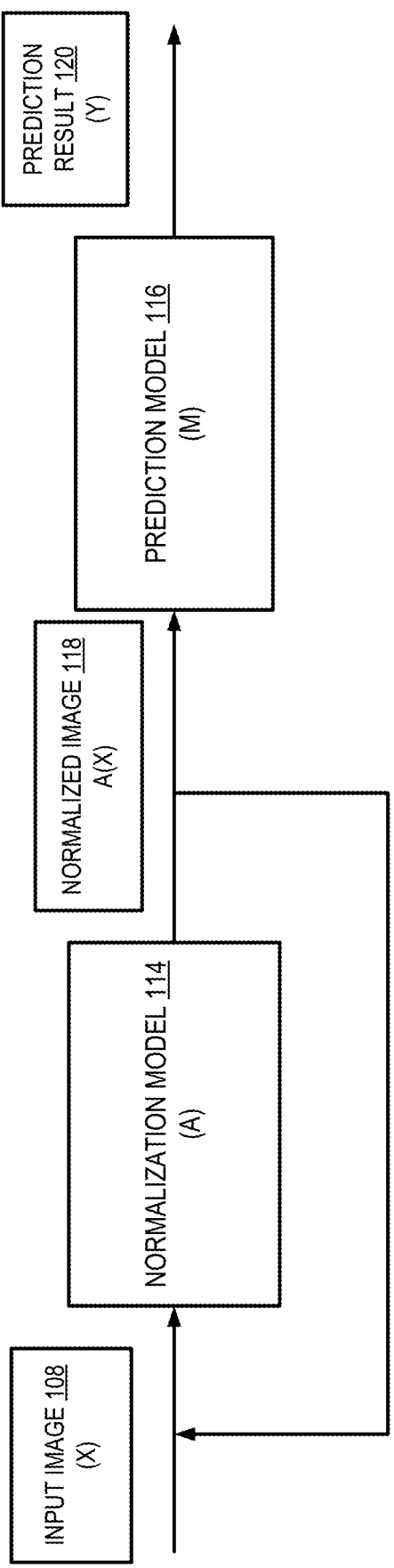
FIG. 2 is a block diagram showing an example architecture of a combination of a normalization model and a prediction model that are jointly trained and utilized, according to certain aspects of the present disclosure.

FIG. 2 shows a block diagram illustrating an example architecture of the combination of the normalization model 114 and the prediction model 116, according to certain aspects of the present disclosure. In the example shown in FIG. 2, the normalization model 114 is concatenated with the prediction model 116 and the output of the normalization model 114 is fed into the prediction model 116 to generate the prediction result. In this way, the input data of the prediction model 116 become a normalized image 118 instead of the original input image 108. Denote the input image as X, and the prediction result as Y. The normalized input image can be represented as $A(X)$, where $A(\cdot)$ denotes the normalization operations performed by the normalization model 114 on the input X. Further, denote the prediction operation performed by the prediction model 116 as $M(\cdot)$, the prediction result Y becomes $Y=M(A(X))$.

During the joint training of the normalization model 114 and the prediction model 116, in order to train the normalization model 114 for the idempotence property, the normalization model 114 may be applied to the input image X multiple times. For example, if the normalization model 114 is applied on the input image X twice, the generated output becomes A(A(X)) and the prediction result made based on this normalized input image becomes M(A(A(X))). With these notations, the idempotence property of a normalization model 114 can be expressed as M(A(A(X)))=M(A(X)).

To enforce the idempotence property of the normalization model 114, an idempotence loss term D (M(A(A(X))), M(A(X))) can be introduced during the training Here, D(A, B) is a distance function measuring the distance between A and B. For instance, D(A,B) can represent the mean absolute error or mean square error between A and B or other distance measurements such as the Kullback-Leibler divergence. In some examples, the selection of the distance function D(A, B) depends on the prediction task. For a classification task, Kullback-Leibler divergence can be used as the distance function. For a segmentation task, the mean absolute error or mean square error can be used. By minimizing a loss function containing this idempotence loss term, the normalization model 114 can be trained to be an idempotent operation (or having the idempotence property) in the context of the specific learning task defined by the prediction model 116.

The loss function for the joint training can further include a loss term based on the prediction result Y=M(A(X)). For example, this loss term can be defined as the entropy of the prediction results, denoted as Entropy(M(A(x)). This loss term can force the combined model (the normalization model 114 and the prediction model 116) to output a confident prediction (a sharp and localized prediction probability distribution) by minimizing the entropy of the prediction results. In some examples, the idempotence loss term and the entropy loss term are defined based on the unlabeled training samples.

For labeled training samples, an additional loss term can be defined for the generated prediction results and the training outputs or labels using any loss term known in the art, such as the mean absolute error loss or mean square error loss. The loss terms for the labeled training samples and the unlabeled training samples can be combined to form the loss function of the training. For example, the loss function of the joint training of the normalization model 114 and prediction model 116 can include a weighted combination of the loss terms for the two types of training data as follows:

$$L = w_1(D(M(A(A(\hat{X}))), M(A(\hat{X}))) + L_1(M(A(\hat{X}))) + w_2 L_2(M(A(\overline{X})), \overline{Y}). \quad (1)$$

Here, $\hat{X}$ is the training inputs contained in the unlabeled training samples; $\overline{X}$ and $\overline{Y}$ are the training inputs and training outputs contained in the labeled training samples, respectively. $w_1$ and $w_2$ are the weights of the loss terms for the unlabeled training samples and labeled training samples, respectively. $D(M(A(A(\hat{X}))), M(A(\hat{X})))$ is the idempotence loss term and $L_1$ $(M(A(\hat{X})))$ is the loss term based on the prediction results for the unlabeled training samples. $L_2(M(A(\hat{X})), \overline{Y})$ is the loss term for the labeled training samples.

The joint training of the normalization model 114 and the prediction model 116 includes iterative operations to find a set of parameters for both models (e.g., weights of nodes in various layers of a neural network, the locations of different layers in the neural network, etc.) that minimize the loss function L. Each iteration can involve finding a set of parameters for the normalization model 114 and prediction model 116 so that the value of the loss function L using the set of parameters is smaller than the value of the loss function L using another set of parameters in a previous iteration. Once the set of parameters are identified, the normalization model 114 and the prediction model 116 have been trained and can be utilized for prediction as designed.

It should be understood that although the loss function in Eqn. (1) above uses a weighted combination of the loss terms for the labeled training samples and unlabeled training samples, any other way for combining the loss terms for the labeled training samples and unlabeled training samples in a semi-supervised training can be utilized. In addition, although both the idempotence loss term D and the loss term $L_1$ are used in Eqn. (1), the loss function L can be constructed using only the idempotence loss term for the unlabeled training samples.

In examples, the normalization model 114 can be a machine learning model whose output and the input have the same format so that the output can be fed into the normalization model 114 as input. The prediction model 116 can be a machine learning model constructed depending on the prediction task. For instance, the normalization model 114 can be a UNET model as presented in Ronneberger et al., U-Net: Convolutional Networks for Biomedical Image Segmentation, In MICCAI, pages 234-241. Springer, 2015. The normalization model can also include other models, such as a fully convolutional network, a Mask-RCNN (Region-based convolutional neural network), a residual neural network ("ResNet"), a DeepLab model (as presented in Chen et al., DeepLab: Semantic Image Segmentation with Deep Convolutional Nets, Atrous Convolution, and Fully Connected CRFs, arXiv:1606.00915), a LinkNet (as presented in Chaurasia et al., LinkNet: Exploiting Encoder Representations for Efficient Semantic Segmentation, arXiv: 1707.03718), a pyramid scene parsing network ("PSPNet") (as presented in Zhao et al., Pyramid Scene Parsing Network, arXiv:1612.01105), a multi-path refinement network ("RefineNet") (as presented in Lin et al., RefineNet: Multi-Path Refinement Networks for High-Resolution Semantic Segmentation, arXiv:1611.06612), a SegNet (as presented in Badrinarayanan et al., SegNet: A Deep Convolutional Encoder-Decoder Architecture for Image Segmentation, arXiv:1511.00561), or an efficient neural network ("ENet") (as presented in Paszke et al., ENet: A Deep Neural Network Architecture for Real-Time Semantic Segmentation, arXiv: 1606.02147).

The prediction model 116 can be a machine-learning model, such as a convolutional neural network ("CNN"), e.g. an inception neural network, ResNet or NASNET provided by GOOGLE LLC from MOUNTAIN VIEW, CALIFORNIA, or a recurrent neural network, e.g. long short-term memory ("LSTM") models or gated recurrent units ("GRUs") models. The prediction model 116 can also be any other suitable machine learning model configured to generate prediction results, such as a three-dimensional CNN ("3DCNN"), a dynamic time warping ("DTW") technique, a hidden Markov model ("HMM"), etc., or combinations of one or more of such techniques—e.g., CNN-HMM or MCNN (Multi-Scale Convolutional Neural Network).

To illustrate, an example of using the normalization model 114 and the prediction model 116 to predict a score of disease stage or disease severity for a patient based on an input pathology image of a tissue sample of the patient is discussed below. In this particular example, the objective is to train the prediction model 116 to predict the presence or absence of metastatic lesions in lymph node tissue sample images of a patient based on which the score of disease stage or disease severity can be predicted. Because stain colors can vary in pathology images, these stain color variations present challenges to the prediction models designed to learn and predict disease score from pathology images.

To improve the prediction accuracy of the prediction model 116, the prediction model 116 is extended to include a normalization model 114 configured to normalize the stain colors in the input pathology image. As a result, the normalization model 114 can help with the semi-supervised training of the prediction model 116 by learning to normalize or standardize the input pathology images before these images are processed by the prediction model 116. As such, the prediction model 116 can expect to receive normalized pathology images and need not include operations for normalizing the input images. In this example, the normalization model 114 is a UNET model, and the prediction model 116 is a ResNet model configured for classification tasks.

Before jointly training the normalization model 114 and the prediction model 116, the training samples are split into labeled and unlabeled training samples. For example, the labeled training samples may include whole-slide pathology images with known disease scores. The unlabeled training samples may include whole-slide pathology images (from the same tissue or study) but without known disease scores. In an example implementation, the labeled training samples include 1000 whole-slide hematoxylin-eosin (H&E) images with known labels (positive or negative for metastatic lesions) and the unlabeled training samples include 50000 whole-slide H&E images with unknown labels.

Using the labeled and unlabeled training samples, the semi-supervised training of the normalization model 114 and prediction model 116 can be performed based on the idempotence loss term as described above. For example, the loss terms in Eqn. (1) for the semi-supervised training can be determined as:

$$L_2(M(A(\overline{X})),\overline{Y})=\text{CrossEntropy}(M(A(\overline{X})),\overline{Y}), \quad (2)$$

$$D(M(A(A(\hat{X}))),M(A(\hat{X})))=KL(M(A(\hat{X})),M(A(A(\hat{X})))), \quad (3)$$

$$L_1(M(A(\hat{X})))=\text{Entropy}(M(A(\hat{X}))). \quad (4)$$

Here, CrossEntropy(M(A($\overline{X}$)),$\overline{Y}$) represents the cross entropy between the predicted results M(A($\overline{X}$)) and the labeled score $\overline{Y}$ in the training samples. KL(•) represents the Kullback-Leibler divergence and Entropy (M(A($\hat{X}$))) represents the entropy of the generated prediction results. By minimizing the loss function L defined using the above loss terms, the trained normalization model 114 and prediction model 116 can be obtained.

In further examples, the trained prediction model 116 can be utilized to generate normalized training samples for a second prediction model that relies on the same or similar features as the prediction model 116. For example, the prediction model 116 is a machine learning model configured for nucleus segmentation in an input pathology image which requires pixel-level prediction. The second prediction model can be a machine learning model configured for predicting the number of nuclei in an input pathology image. In this example, the features used by the prediction model 116 for segmenting the nucleus (e.g., the edge information) are similar to the features used by the second machine learning model for predicting the number of nuclei in the input pathology image. As such, the normalization model 114 trained jointly with this prediction model 116 can be utilized to generate normalized training samples for the second prediction model by applying the normalization model 114 on the set of training samples for the second prediction model. These normalized training samples can then be used to train the new prediction model. In this case, the second prediction model is trained alone without a normalization model. During the prediction, the normalization model 114 is used in conjunction with the second prediction model. In other words, an input image is normalized by the normalization model 114 before being sent to the second prediction model for prediction.

In the above example, the second prediction model can also be a machine learning model configured to predict the cancer stage based on the nuclei distribution in the input pathology image, or a machine learning model configured to predict the presence of metastatic lesions in the input image, which is based on the size and shape of the nuclei. These two models also utilize the features similar to the prediction model 116 for the prediction. As such, the normalization model 114 can also be utilized to generate normalized training data for these two models. As such, once trained, the normalization model 114 can be re-used to generate normalized training data for other prediction models and allowed these prediction models to be trained with high accuracy but using less training data than what would be required had there been no normalization performed on the training data.

According to the above, for a given prediction model 116, to normalize training inputs, there are two options. The first option is to expand the prediction model 116 to include or concatenate with a normalization model 114 and jointly train the normalization model 114 and the prediction model 116. The second option is to use a pre-trained normalization model 114 (trained jointly with another prediction model 116) to generate the normalized training samples. The prediction model 116 is then trained alone with the normalized training samples. The first option allows the normalization model 114 to be customized to the prediction model 116 thereby performing the normalization more suitable to the prediction model 116. The second option allows the prediction model 116 to be trained using a smaller amount of training data. In some examples, the decision of selecting option one or option two can be made according to the available training samples. If the prediction model 116 has a sufficient number of training samples, a normalization model 114 can be combined with the prediction model 116 and jointly trained. If the prediction model 116 has an insufficient number of training samples, a normalization model 114 trained jointly with another prediction model that relies on similar features as the prediction model 116 can be utilized to generate the normalized training data to train the prediction model 116.

Figure 3:
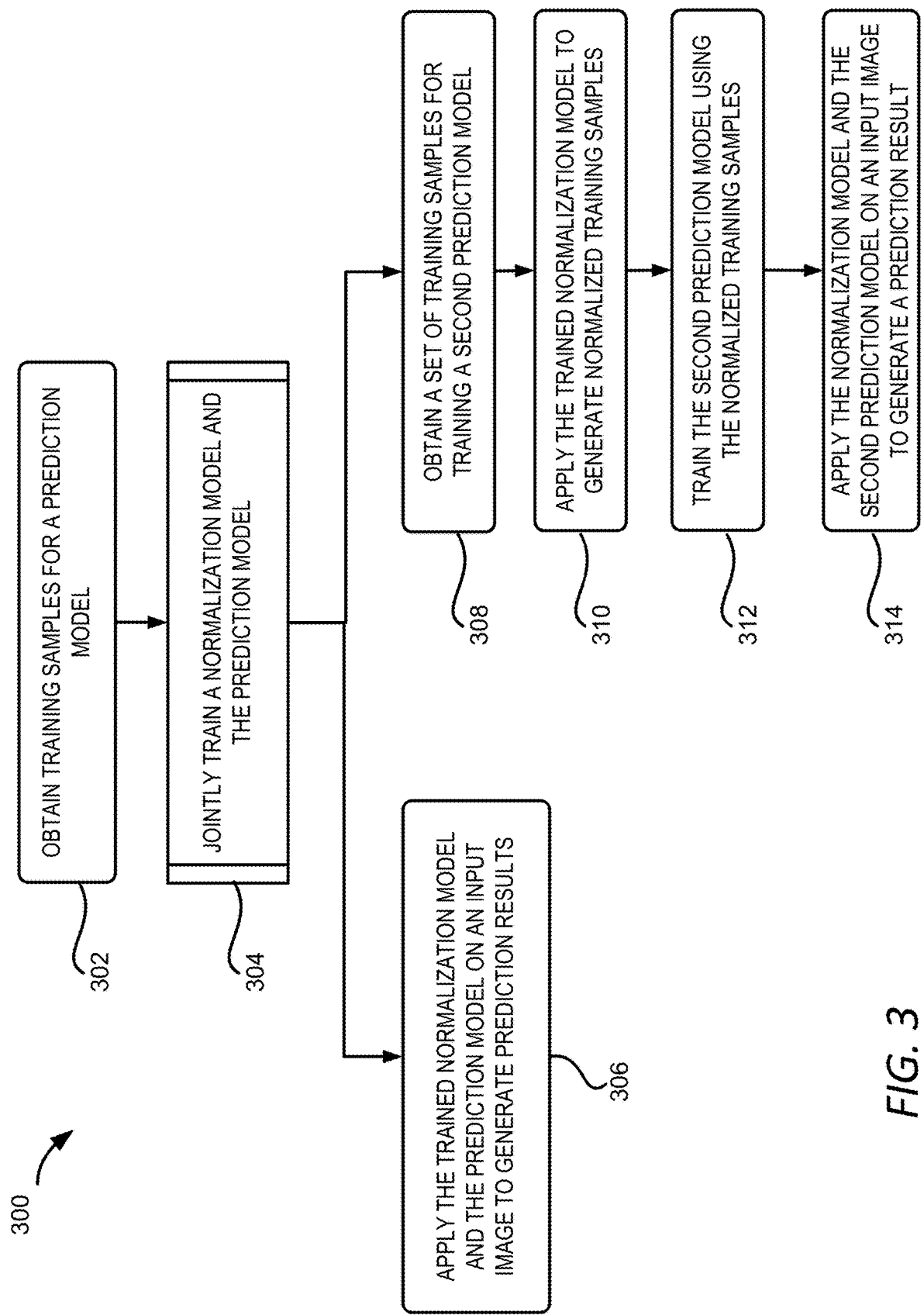
FIG. 3 shows an example of a method for training and utilizing a normalization model along with a prediction model to make predictions, according to certain aspects of the present disclosure.

Referring now to FIG. 3, where an example of a process 300 for using a normalization model 114 in conjunction with a prediction model 116 to generate prediction results is presented. The example process 300 will be discussed with respect to the example environment 100 shown in FIG. 1 and the example model architecture shown in FIG. 2, but may be employed according to any suitable system according to this disclosure. One or more computing devices (e.g., the computing system 102) implement operations depicted in FIG. 3 by executing suitable program code (e.g., the prediction system 104 or the model training system 106).

At block 302, the process 300 involves obtaining training samples 112 for a prediction model 116. As discussed above with regard to FIG. 1, the training samples 112 can be stored in a datastore 110 and include labeled training samples and unlabeled training samples. A labeled training sample includes a training input and a corresponding training output or label describing what the prediction should be, whereas an unlabeled training sample includes the training input, but does not include the corresponding training output or label. At block 304, the process 300 involves adding a normalization model 114 to the prediction model 116 and jointly training the normalization model 114 and the prediction model 116. An example process of training the normalization model 114 to the prediction model 116 is presented below with regard to FIG. 4.

At block 306, the process 300 involves applying the trained normalization model 114 and prediction model 116 to perform the prediction. As discussed in detail above with respect to FIGS. 1 and 2, for a given input image 108, the normalization model 114 is applied to generate the normalized input image 118. The normalized input image 118 is then fed into the prediction model 116 to generate the prediction result 120.

As discussed above with respect to FIG. 2, in some implementations, the trained normalization model 114 is used to train another prediction model which is then used to generate the prediction results based on input images. Blocks 308-314 shows this implementation. At block 308, the process 300 involves obtaining another set of training samples. This second set of training samples is for training a second prediction model and can also be stored in the datastore 110. Similar to the training samples obtained at block 302, this second set of training samples may also include labeled training samples and unlabeled training samples. The labels in the labeled training samples correspond to the prediction results of the second prediction model.

At block 310, the process 300 involves applying the normalization model 114 trained in block 304 to the second set of training samples (i.e., the training samples for the second prediction model) to generate normalized training samples. The normalized training samples can be stored in the datastore 110. At block 312, the process 300 involves training the second prediction model using the normalized training samples generated at block 310. The training can be performed using any existing semi-supervised training based on the normalized training samples. After the second prediction model is trained, the process 300 involves, at block 314, applying the trained normalization model and the trained second prediction model to make predictions based on input images. In particular, for a given input image, the normalization model 114 is used to generate a normalized input image, and then the second prediction model is applied to the normalized input image to generate the prediction result.

Figure 4:
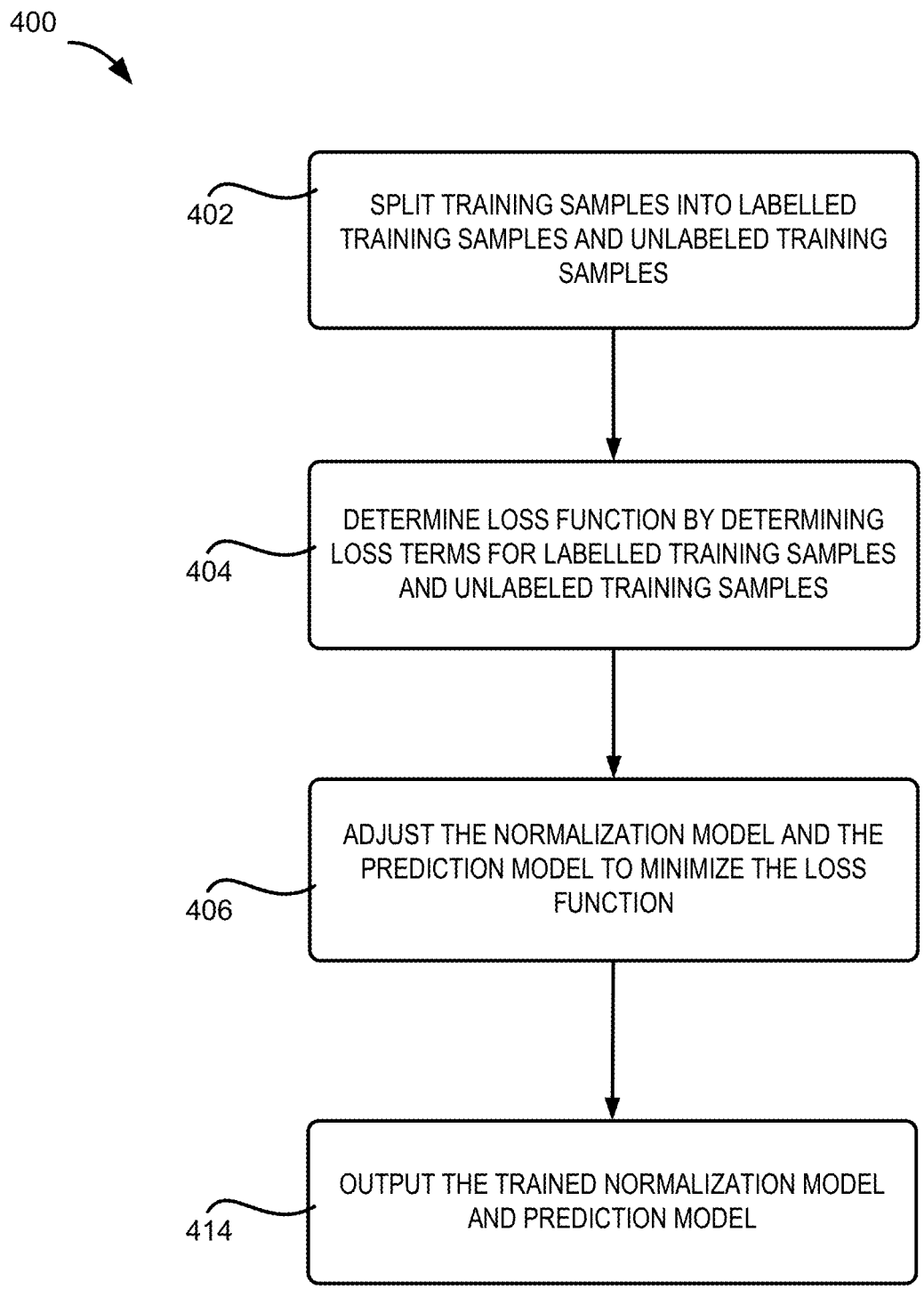
FIG. 4 shows an example of a method for jointly training a normalization model and a prediction model, according to certain aspects of the present disclosure.

Referring now to FIG. 4, where an example of a process 400 for jointly training a normalization model 114 and a prediction model 116 is presented. The example process 400 will be discussed with respect to the example environment 100 shown in FIG. 1 and the example model architecture shown in FIG. 2, but may be employed according to any suitable system according to this disclosure. One or more computing devices (e.g., the computing system 102) implement operations depicted in FIG. 4 by executing suitable program code (e.g., the model training system 106). The process 400 can be utilized to implement block 304 in FIG. 3.

At block 402, the process 400 involves splitting the training samples 112 for the prediction model 116 into labeled training samples and unlabeled training samples. The labeled training samples and unlabeled training samples will be used to calculate separate loss terms in a loss function used for the training.

At block 404, the process 400 involves determining the loss function of the joint training. As discussed in detail above with regard to FIG. 2, the loss function includes loss terms for labeled training samples and unlabeled training samples. In particular, the loss terms for the unlabeled training samples include an idempotence loss term. For example, the idempotence loss term can be defined as a term measuring the difference between a first set of prediction results and a second set of prediction results generated by the prediction model, such as $D(M(A(A(\hat{X}))), M(A(\hat{X})))$ shown in Eqn. (1). The first set of prediction results are generated using a first set of normalized training inputs generated by applying the normalization model 114 to training inputs in the unlabeled training samples once. The second set of prediction results are generated using a second set of normalized outputs generated by applying the normalization model 114 to the training inputs more than once.

In another example, the idempotence loss term can be defined as $D(A(A(\hat{X})), A(\hat{X}))$, which measures the difference between the normalized training inputs generated by the normalization model 114 once, $A(\hat{X})$, and the normalized training inputs generated by the normalization model 114 twice, $A(A(\hat{X}))$. In this example, the idempotence loss term does not depend on the prediction model 116. As discussed above with respect to FIG. 2, $D(A,B)$ is a distance function measuring the distance between A and B. For instance, $D(A,B)$ can represent the mean absolute error or mean square error between A and B or other distance measurements such as the Kullback-Leibler divergence. In some examples, the selection of the distance function $D(A,B)$ depends on the prediction task. For a classification task, Kullback-Leibler divergence can be used as the distance function. For a segmentation task, the mean absolute error or mean square error can be used.

The loss terms for the unlabeled training samples can also include a loss term defined on the prediction results of the prediction model 116 $L_1(M(A(\hat{X})))$, such as an entropy loss term shown in Eqn. (4). By including the entropy loss term in the loss function, the prediction model 116 can be trained to generate a localized prediction probability distribution instead of a uniform distribution. The loss term for the labeled training samples $L_2(M(A(\hat{X})), \overline{Y})$ can be defined using any loss term known in the art, such as the cross entropy loss term defined in Eqn. (2). The loss terms for the labeled training samples and unlabeled training samples can be combined, such as through a weighted combination, to generate the loss function for the training.

At block 406, the process 400 involves adjusting the parameters of the normalization model 114 and the prediction model 116 to minimize the loss function. Depending on the type of the normalization model 114 and the prediction model 116, the parameters can include, for example, weights of nodes in various layers of a neural network, the locations of different layers in the neural network, and so on. The adjustments may be performed by using training algorithms such as the backpropagation algorithm. At block 408, the process 400 involves outputting the trained normalization model 114 and the prediction model 116.

Figure 5:
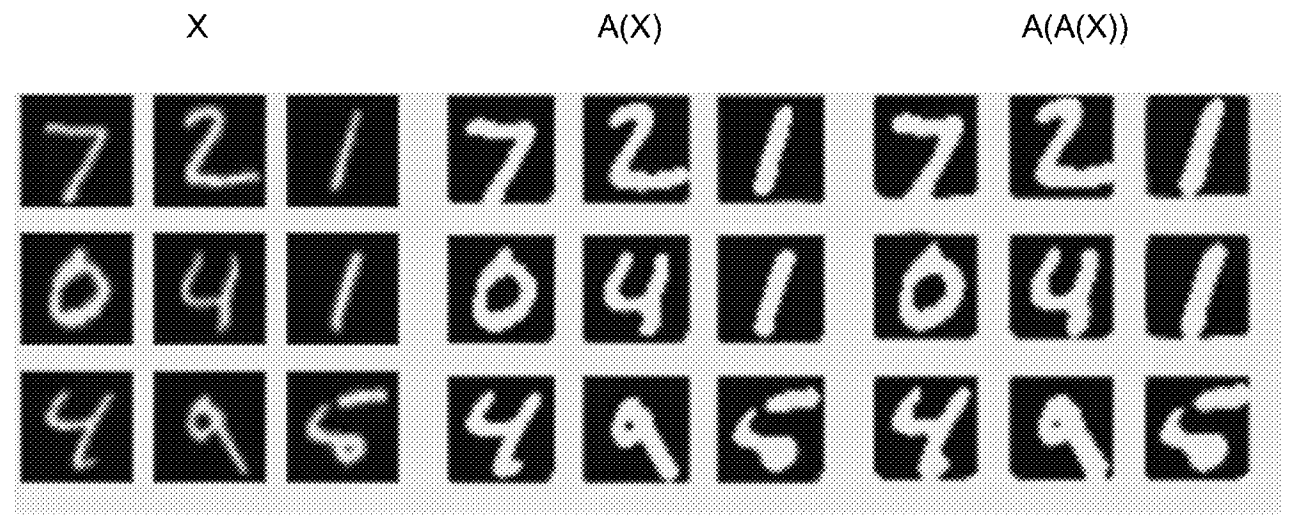

FIG. 5 shows examples of input images (MNIST images) for a prediction model configured for predicting the number contained in an input image. FIG. 5 also shows the normalized input images generated by applying a trained normalization model to the input images. The left group of images shows the input images each containing a single digit. Each of these images is a grayscale image and contain gray pixels and textures near the edges of the digit contained in the image. The middle group of images includes the normalized images by applying the normalization model once. In these normalized images, irrelevant features are removed. For example, the gray pixels are normalized to black or white pixels and the textures near the edge areas are removed. In addition, the edges of the digits, which are features used by the prediction model to predict the number contained in the image, are highlighted. The right group of images includes the normalized images by applying the normalization model on the input images twice. These normalized images are substantially similar to the middle group of normalized images. This indicates that the normalization model has been trained to have idempotence property.

It should be understood that while the above description focus on images as input to the normalization model 114 and the prediction model 116, the technology presented herein applies to any type of input data, such as time-series data (e.g., text or speech) or structured data (e.g., demographic data or poll results). Furthermore, although the normalization model 114 is described as a separate model from the prediction model 116, the normalization model can be merged into the prediction model 116. For example, the prediction model 116 can be expanded to include one or more layers or blocks near the input and to enforce the idempotence on these layers or blocks during the training. Other ways of merging the normalization model 114 into the prediction model 116 may be implemented.

Figure 6:
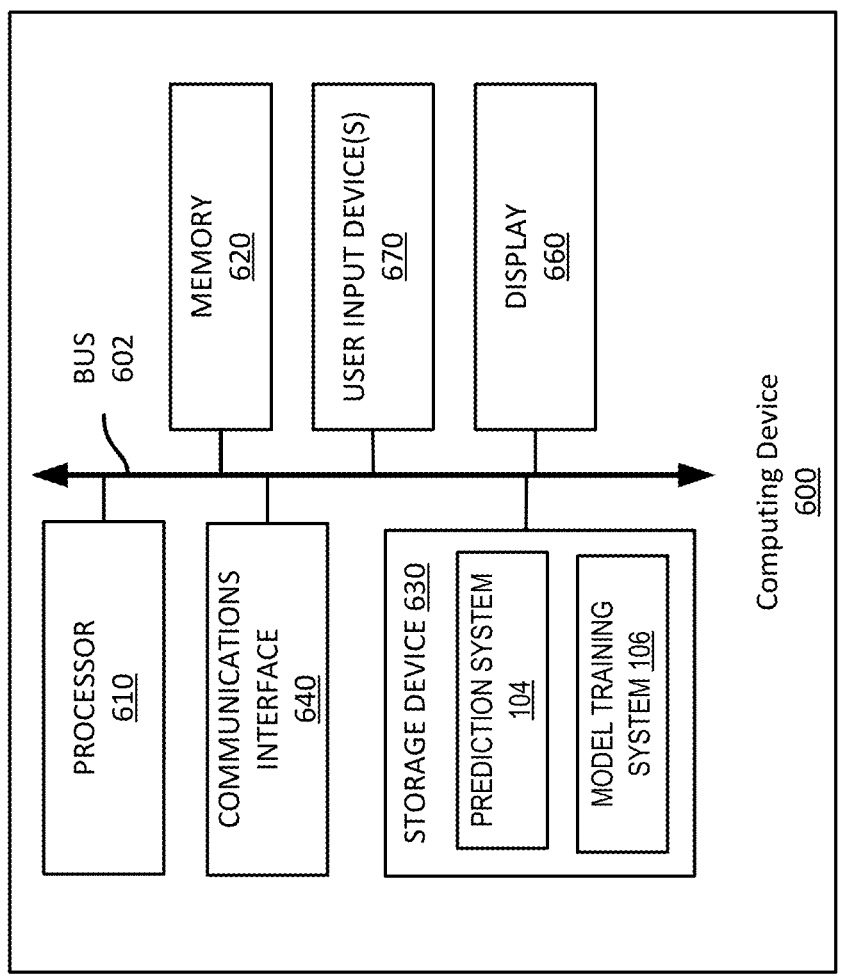
FIG. 6 shows an example of a computing device suitable for implementing aspects of the techniques and technologies presented herein.

Referring now to FIG. 6, FIG. 6 shows an example computing device 600 suitable for use in example systems or methods for training and using a prediction model jointly with a normalization model to provide prediction results. The example computing device 600 includes a processor 610 which is in communication with the memory 620 and other components of the computing device 600 using one or more communications buses 602. The processor 610 is configured to execute processor-executable instructions stored in the memory 620 to perform machine learning model training and prediction according to different examples, such as part or all of the example processes 300 and 400 described above with respect to FIGS. 3 and 4. The computing device, in this example, also includes one or more user input devices 670, such as a keyboard, mouse, touchscreen, microphone, etc., to accept user input. The computing device 600 also includes a display 660 to provide visual output to a user.

The computing device 600 can include or be connected to one or more storage devices 630 that provides non-volatile storage for the computing device 600. The storage devices 630 can store system or application programs and data utilized by the computing device 600, such as modules implementing the functionalities provided by the prediction system 104 or the model training system 106. The storage devices 630 might also store other programs and data not specifically identified herein.

The computing device 600 also includes a communications interface 640. In some examples, the communications interface 640 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically configured hardware, such as field-programmable gate array (FPGA) specifically to execute the various methods. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example, non-transitory computer-readable storage media, that may store instructions that, when executed by the processor, can cause the processor to perform the steps described herein as carried out, or assisted, by a processor. Examples of non-transitory computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A computer-implemented method, comprising:
receiving an input image of a tissue sample of a patient;
generating a normalized image by applying a normalization model on the input image, wherein the normalization model is configured to generate normalized data using input data for a prediction model, the prediction model configured to generate prediction results using normalized data generated by the normalization model, and wherein the normalization model and the prediction model are jointly trained by comparing a first set of prediction results generated by the prediction model using a first set of normalized training inputs generated by applying the normalization model to training inputs in a set of training samples once and a second set of prediction results generated by the prediction model using a second set of normalized training inputs generated by applying the normalization model to the training inputs more than once; and
generating a prediction of disease severity for the patient by applying the prediction model on the normalized image.

2. The method of claim 1, wherein the normalization model and the prediction model are jointly trained based on a loss function comprising an idempotence loss term measuring a difference between the first set of prediction results and the second set of prediction results.

3. The method of claim 2, wherein the set of training samples comprise unlabeled samples that comprise the training inputs without corresponding training outputs, and wherein the idempotence loss term is calculated based on the training inputs in the unlabeled samples.

4. The method of claim 3, wherein the set of training samples further comprises labeled samples that comprise training inputs and corresponding training outputs, and wherein the loss function further comprises a loss term for the labeled samples measuring a difference between prediction results generated by the prediction model and the normalization model based on the training inputs and the corresponding training outputs.

5. The method of claim 2, wherein the idempotence loss term comprises a Kullback-Leibler divergence between the first set of prediction results and the second set of prediction results, a mean absolute error between the first set of prediction results and the second set of prediction results, or a mean square error between the first set of prediction results and the second set of prediction results.

6. The method of claim 2, wherein the loss function further comprises an entropy loss term representing an entropy of the first set of prediction results or the second set of prediction results.

7. The method of claim 6, wherein the input image is a pathology image and generating the prediction of disease severity for the patient comprises detecting presence or absence of metastatic lesions in the pathology image using the prediction model.

8. A system comprising:
at least one processor; and
at least one non-transitory computer-readable medium comprising processor-executable instructions stored thereupon, which, when executed by the at least one processor, cause the processor to:
receive an input image of a tissue sample of a patient;
generate a normalized image by applying a normalization model on the input image, wherein the normalization model is configured to generate normalized data using input data for a prediction model, the prediction model configured to generate prediction results using normalized data generated by the normalization model, and wherein the normalization model and the prediction model are jointly trained by comparing a first set of prediction results generated by the prediction model using a first set of normalized training inputs generated by applying the normalization model to training inputs in a set of training samples once and a second set of prediction results generated by the prediction model using a second set of normalized training inputs generated by applying the normalization model to the training inputs more than once; and
generate a prediction of disease severity for the patient by applying the prediction model on the normalized image.

9. The system of claim 8, wherein the normalization model and the prediction model are jointly trained based on a loss function comprising an idempotence loss term measuring a difference between the first set of prediction results and the second set of prediction results.

10. The system of claim 9, wherein the set of training samples comprise unlabeled samples that comprise the training inputs without corresponding training outputs, and wherein the idempotence loss term is calculated based on the training inputs in the unlabeled samples.

11. The system of claim 10, wherein the set of training samples further comprises labeled samples that comprise training inputs and corresponding training outputs, and wherein the loss function further comprises a loss term for the labeled samples measuring a difference between prediction results generated by the prediction model and the normalization model based on the training inputs and the corresponding training outputs.

12. The system of claim 9, wherein the idempotence loss term comprises a Kullback-Leibler divergence between the first set of prediction results and the second set of prediction results, a mean absolute error between the first set of prediction results and the second set of prediction results, or a mean square error between the first set of prediction results and the second set of prediction results.

13. The system of claim 9, wherein the loss function further comprises an entropy loss term representing an entropy of the first set of prediction results or the second set of prediction results.

14. The system of claim 13, wherein the input image is a pathology image and generating the prediction of disease severity for the patient comprises detecting presence or absence of metastatic lesions in the pathology image using the prediction model.

15. A non-transitory computer-readable medium comprising processor-executable instructions to cause a processor to:
receive an input image of a tissue sample of a patient;
generate a normalized image by applying a normalization model on the input image, wherein the normalization model is configured to generate normalized data using input data for a prediction model, the prediction model configured to generate prediction results using normalized data generated by the normalization model, and wherein the normalization model and the prediction model are jointly trained by comparing a first set of prediction results generated by the prediction model using a first set of normalized training inputs generated by applying the normalization model to training inputs in a set of training samples once and a second set of prediction results generated by the prediction model using a second set of normalized training inputs generated by applying the normalization model to the training inputs more than once; and generate a prediction of disease severity for the patient by applying the prediction model on the normalized image.

16. The non-transitory computer-readable medium of claim 15, wherein the normalization model and the prediction model are jointly trained based on a loss function comprising an idempotence loss term measuring a difference between the first set of prediction results and the second set of prediction results.

17. The non-transitory computer-readable medium of claim 16, wherein the set of training samples comprise unlabeled samples that comprise the training inputs without corresponding training outputs, and wherein the idempotence loss term is calculated based on the training inputs in the unlabeled samples.

18. The non-transitory computer-readable medium of claim 17, wherein the set of training samples further comprises labeled samples that comprise training inputs and corresponding training outputs, and wherein the loss function further comprises a loss term for the labeled samples measuring a difference between prediction results generated by the prediction model and the normalization model based on the training inputs and the corresponding training outputs.

19. The non-transitory computer-readable medium of claim 16, wherein the idempotence loss term comprises a Kullback-Leibler divergence between the first set of prediction results and the second set of prediction results, a mean absolute error between the first set of prediction results and the second set of prediction results, or a mean square error between the first set of prediction results and the second set of prediction results.

20. The non-transitory computer-readable medium of claim 16, wherein the loss function further comprises an entropy loss term representing an entropy of the first set of prediction results or the second set of prediction results.

\* \* \* \* \*